(12) United States Patent
Cook et al.

(10) Patent No.: US 10,390,717 B2
(45) Date of Patent: Aug. 27, 2019

(54) TISSUE VARIABILITY COMPENSATION APPARATUS AND METHOD

(71) Applicant: HUNTLEIGH TECHNOLOGY LIMITED, Bedfordshire (GB)

(72) Inventors: Stephen John Cook, Hampshire (GB); Francis Gregory Baily, Cardiff (GB); Philip Morris, Cardiff (GB); Nigel A J Gough, Rhonda Cynon Taff (GB)

(73) Assignee: Huntleigh Technology Limited (GB)

( * ) Notice: Subject to any disclaimer, the term of this patent is extended or adjusted under 35 U.S.C. 154(b) by 330 days.

(21) Appl. No.: 15/365,635

(22) Filed: Nov. 30, 2016

(65) Prior Publication Data

US 2017/0079536 A1 Mar. 23, 2017

Related U.S. Application Data

(63) Continuation-in-part of application No. PCT/GB2015/051563, filed on May 29, 2015.

(30) Foreign Application Priority Data

May 30, 2014 (GB) .................................. 1409599.6

(51) Int. Cl.
| | |
|---|---|
| A61B 5/024 | (2006.01) |
| A61B 5/00 | (2006.01) |
| A61B 5/1495 | (2006.01) |
| A61B 5/1455 | (2006.01) |
| A61B 5/02 | (2006.01) |
| G16H 40/63 | (2018.01) |

(52) U.S. Cl.
CPC ........ *A61B 5/02433* (2013.01); *A61B 5/0017* (2013.01); *A61B 5/1495* (2013.01); *A61B 5/14551* (2013.01); *A61B 5/7203* (2013.01); *A61B 5/725* (2013.01); *A61B 5/7214* (2013.01); *A61B 5/7225* (2013.01); *A61B 5/7228* (2013.01); *A61B 5/7257* (2013.01); *A61B 5/02007* (2013.01); *A61B 5/02416* (2013.01); *A61B 5/6828* (2013.01); *A61B 2562/0233* (2013.01); *G16H 40/63* (2018.01)

(58) Field of Classification Search
None
See application file for complete search history.

(56) References Cited

U.S. PATENT DOCUMENTS

| | | | | |
|---|---|---|---|---|
| 4,848,901 A | * | 7/1989 | Hood, Jr. | ........... A61B 5/02433 356/41 |
| 2004/0204638 A1 | | 10/2004 | Diab et al. | |
| 2008/0076984 A1 | * | 3/2008 | Gough | ................. A61B 5/0059 600/310 |
| 2011/0071366 A1 | * | 3/2011 | McKenna | ........... A61B 5/14551 600/300 |
| 2016/0081602 A1 | * | 3/2016 | Lisogurki | .......... A61B 5/14551 600/476 |

FOREIGN PATENT DOCUMENTS

GB 2419403 A 4/2006

* cited by examiner

*Primary Examiner* — John C Kuan
(74) *Attorney, Agent, or Firm* — The Webb Law Firm (57) ABSTRACT

A method and apparatus of compensating for a differential error between a plurality of body surface sensors, where each sensor respectively comprises a transmitter and a receiver.

16 Claims, 4 Drawing Sheets

TISSUE VARIABILITY COMPENSATION APPARATUS AND METHOD

CROSS-REFERENCE TO RELATED APPLICATIONS

This is a continuation-in-part of International Patent Application No. PCT/GB2015/051563, filed on May 29, 2015, pursuant to 35 USC 365(c), which in turn claims benefit of priority to Great Britain Application No. 1409599.6, filed on May 30, 2014; the entire disclosures of all the above applications are expressly incorporated by reference herein.

FIELD OF ART

The present disclosure is in the field of medical technology where acquiring physiological signals from a patient (whether human or animal) for subsequent diagnostic interpretation is by the use of non-invasive body surface sensors. These may be separate transmitters and receivers or may have both functions combined into one physical transducer. The sensors may be optical, in which case, the wavelengths used may be either visible or non-visible. In the latter case, they often fall into the infrared spectrum. This type of sensor may have a data connection to downstream data capture and manipulation equipment via an electrical cable or a wireless interface of one of many kinds, such as optical, radio, acoustic, magnetic field, etc.

BACKGROUND

The present disclosure concerns an apparatus and method for compensating for variations in the overall transfer ratio from transmitter input to receiver output between two or more sensors mounted at different anatomical locations. This includes variations due to overall changes in path length arising from different equivalent transmission characteristics through different body locations. Though also suitable for many other skin contact sensors using non-optical transduction principles, such as RF, magnetic field, electric field or vibration, the apparatus and method will be illustrated below by the example of an infrared (IR) wavelength transducer combining receiver and transmitter functions, which can be attached to the lower limbs of a patient.

Physically, a typical non-invasive optical transducer will consist of a cylindrical body with a slightly larger circular base. The base contains two small circular apertures within which are the tips of infrared transmitter and receiver devices. These are spaced apart with a centre-to-centre distance of a few mm.

For correct operation, the transducer base needs to be in accurate contact with the skin of a patient. This enables a beam of infrared energy to enter the skin and surface tissues to a depth in excess of 2 mm. Random photon to photon scattering within the beam enables a much attenuated signal to be gathered by the receiver device. The transmission path of the photons within the received signal has passed through both the capillary loops and subsurface horizontal structure of small veins and arteries which lies around 2 mm below the skin in a normal healthy adult human.

The overall transmission attenuation from transmitter to receiver is composed of several elements, including backscatter and absorption by various anatomical structures such as tissue, ligament etc. That part of the transmitted intensity which reaches sub-surface blood vessels is further reduced by blood volume related absorption and therefore by the time-dependent quantity of blood in both arterial and venous elements of the vasculature.

However the physical spacing of the transmitter and receiver devices is such that the received signal is dominated by the blood volumes in the micro-circulation, rather than the larger and deeper veins and arteries. Processing of this received micro-circulation dependent signal in the time and frequency domains can reveal many valuable items of information, which correlate with diseases of both the vasculature and the peripheral nervous system.

There are several components to the IR energy exiting the tissue which is picked up in the receiver device of the transducer, as follows:
(a) absorption by pulsating and non-pulsating arterial blood, typically 1% to 2% of the total;
(b) absorption by venous blood and other tissue, typically <20% of the total; and
(c) scattering and reflection of incident light, typically >80% of the total.

In pulse oximetry, only the signal element dependent on pulsating arterial blood is important and the first processing step is to normalise this by dividing by the "dc" component of the received signal which is composed of all the other elements listed above. Averaging a period of received signal or passing the complete signal through a low-pass filter set to remove frequencies above, say, 0.05 Hz will produce a signal value representing the overall effect of scattering and reflection, tissue absorption, non-pulsatile arterial blood absorption, non-time dependent venous blood absorption and averaged low frequency vasomotor time dependent venous blood absorption.

Normalising by this "dc" signal provides a result which is unaffected by fluctuations in the incident light intensity and is effectively self-calibrating. Thus variations in scattering and reflection of incident light on entering the skin, as well as the transduction ratios of transmitter and receiver and circuit gain tolerances, do not affect the result.

In the alternative situation where the received signal component of interest comes from the time varying element of the venous blood, this signal is composed of:
(a) a breathing component with energy around the breathing frequency of 5 to 30 breathes per minute; and
(b) lower frequency local and systemic vasomotor effects on venous blood volume at frequencies from about 0.1 Hz down to below 0.01 Hz.

This signal can also be normalised in a similar manner to the pulsatile arterial signal described above.

As before, a normalising value can be produced by averaging a period of received signal, or passing the complete signal through a low-pass filter set to remove frequencies above, say, 0.05 Hz, so producing a signal value representing the overall effect of scattering and reflection, tissue absorption, non-pulsatile arterial blood absorption, non-time dependent venous blood absorption and averaged low frequency vasomotor time dependent venous blood absorption.

However, there are also applications where important physiological information is contained in the amplitude of the breathing signal frequency range of venous blood volume variation. In particular, consider an application where a significant amplitude difference in this frequency range, when comparing a pair of transducers in different anatomical locations, is indicative of a certain physiological condition. For example, the transducer pair may be located on contralateral parts of the body, such as the left and right upper arms, or the transducers may be mounted on left and right legs below the knee, where the physiological condition of interest may for instance be a lower limb DVT, either above or below the knee.

In such a case, the standard method of normalisation with the "dc" signal value described above introduces some problems. The frequency ranges of interest for vasomotor and breathing effects overlap with each other, so an ideal "dc" signal cannot be produced, containing the former with none of the latter, or vice versa. In addition accurate averaging of such low vasomotor frequencies requires long data records, which may not be available or consistent with a short diagnostic process.

The aim of such normalisation is to remove any effect on signals which does not affect each signal in the pair in the same way. Such differences may be in electronic hardware tolerances, sensor location or anatomy, as follows.

Hardware tolerances include:
(a) tolerances in overall circuit gain, including optical transmitter and receiver transduction ratios;
(b) tolerances in analogue filter frequency responses, particularly the low frequency high-pass "dc" level removing filter; and
(c) variations with time and temperature in these parameters, which are different between transducers.

Sensor location differences include:
(a) skin areas with differing amounts of hair;
(b) kin conditions on one leg which require the constant use of creams or moisturisers which include certain dermatological conditions and skin drying caused by long term use of anti-coagulants; and
(c) medical conditions on one leg which cause stretching of the skin at the transducer location such as oedema or the swelling associated with post phlebotic syndrome.

Anatomical differences between contra-lateral sites include:
(a) varying pigmentation;
(b) varying degrees of healed scar tissue from leg or pressure ulcers or other wounds; and
(c) variations in tissue attenuation caused by natural tolerances in tissue structures.

There may also be other problems which affect only one signal of a pair on a momentary basis, such as involuntary patient movement which brings the transducer into contact with other surfaces. Cabled transducers can also suffer from tension problems due to cable weight and stiffness and inevitable cable snags, as well as tension variations created by involuntary patient movement.

Note that in this latter case, for an asymmetric momentary problem, the averaging or filtering involved in producing a "dc" signal value will generate an asymmetric error which is impossible to remove. Conventionally, such an error can only be prevented by using a sophisticated pattern recognition algorithm, should one be possible, to identify the occurrence of a problem and remove use of this time slot of data on both signals.

In practice, in order to provide better received signal-to-noise ratios, IR optical transmitters are driven by high level current sources. In order to prevent thermal overload, and consequent thermal runaway and chip destruction, the drive is not continuous, but composed of narrow pulses, typically at a 1 to 3 kHz rate. The transmit pulse modulation signal is used to control a synchronous receiver.

To detect and compensate for any differential error between a plurality of transducer signals, including those listed above, an additional signal is introduced into the system.

SUMMARY

Accordingly, in a first aspect, there is provided an apparatus for compensating for a differential error between a plurality of body surface sensors for acquiring respective physiological signals from a human or animal patient, each such sensor respectively comprising a transmitter, a receiver, and connected to an output of the respective receiver, a charge-to-voltage converter, the apparatus comprising: a timing signal generator comprising an oscillator, to generate a timing signal; a channel for each respective body surface sensor, each channel comprising: (i) a current modulator to receive said timing signal and supply a current drive signal timed by said timing signal to the transmitter of the respective body surface sensor; (ii) a synchronous receiver to receive said timing signal from the timing signal generator and an output signal timed by said timing signal from the charge-to-voltage converter of the respective body surface sensor and supply a broadband output signal; (iii) an analogue high-pass filter to receive the broadband output signal from the synchronous receiver and supply a filtered output signal; and (iv) an anti-aliasing analogue low-pass filter to receive the filtered output signal from the high-pass filter and supply an anti-aliased output signal; the apparatus further comprising: an analogue-to-digital converter to receive the anti-aliased output signal from the respective channels of each respective body surface sensor and supply a digital output signal for downstream signal processing; wherein the timing signal generator also generates a digital representation of a sine wave and comprises a digital-to-analogue converter to receive the digital sine wave representation at an update rate higher than the frequency of the timing signal and convert it into an analogue sine wave having a frequency greater than a highest frequency of the physiological signals and less than a cut-off frequency of the anti-aliasing low pass filter; a low-pass filter to receive the analogue sine wave from the digital-to-analogue converter and remove update rate components therefrom to provide a clean sine wave; and an amplitude modulator to receive the clean sine wave from the low-pass filter and add it to the timing signal.

In a second aspect, there is provided a method of compensating for a differential error between a plurality of body surface sensors, where each sensor respectively comprises a transmitter and a receiver, the method comprising the steps of: adding an amplitude modulated signal to a transmitted signal respectively transmitted by each of said transmitters, the amplitude modulated signal having a frequency: (i) greater than a highest frequency of a physiological signal of a human or animal patient to which the plurality of body surface sensors is applied; and (ii) less than a cut-off frequency of an anti-aliasing low pass filter of an apparatus for processing a received signal respectively received by each of said receivers; applying a band-pass filter to recover the amplitude modulated signal from a plurality of the received signals to provide a respective plurality of compensation signals; comparing the respective amplitudes of the respective plurality of compensation signals with each other; and adjusting the amplitude of at least one of the respective received signals until the amplitudes of the respective plurality of compensation signals are substantially equal to each other.

Since the sine wave frequency is carefully chosen to be outside the frequency range of physiological interest without significantly changing the analogue filter design requirements, it can easily be subjected to downstream signal processing. For instance, 5 Hz or 300 bpm falls above the maximum cardiac range but well within existing anti-aliasing low pass filter performance.

This compensation signal can be recovered in each of the signal paths by digital band-pass filtering to provide respective compensation signals. These signals should be of equal amplitude if all physiological signal effects are symmetrical. If they are not, then the ratio of the amplitudes can be used to correct for asymmetrical physiological effects. Note that this correction is carried out in real time and does not require long term signal averaging. If a temporary but significant time-dependent variation in only one compensation signal is detected then this time slot can be removed from each physiological signal before processing.

As described below, the apparatus and method of the present disclosure is capable of detecting and compensating for errors introduced by asymmetrical effects on two or more optical transducers mounted on different anatomical locations on humans or animals. The compensation is real-time, not relying on low pass filtering or averaging, unlike the current method derived from pulse oximetry signal processing. This real-time nature allows the detection and elimination from downstream processing of signal artefacts which do not occur identically in all sensor signals.

BRIEF DESCRIPTION OF THE DRAWINGS

Further features and advantages of the present apparatus and method will become apparent from the following detailed description, which is given by way of example and with reference to the accompanying drawings, wherein.

DESCRIPTION OF EXEMPLARY EMBODIMENTS

Figure 1:
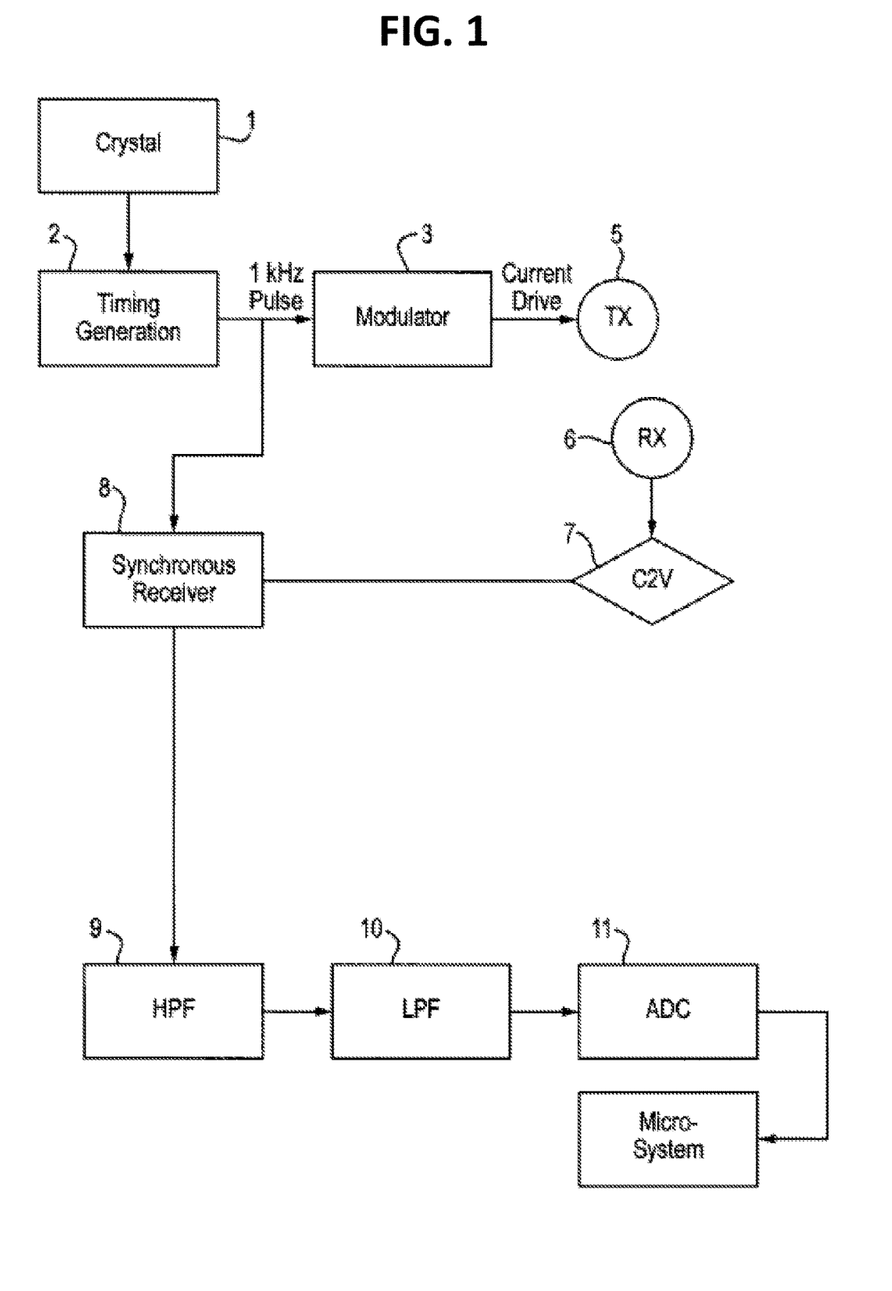
FIG. 1 is a schematic block diagram of the front end of a system excluding detail of a downstream microsystem for signal processing.

Referring firstly to FIG. 1, the overall system can be split into two parts, a front end from transducer to analogue-to-digital convertor (adc) digital output and a downstream microprocessor system implementing signal processing, control panel, display and interfacing tasks.

For simplicity a single channel front end system block diagram is shown. In practice for two or more channels there would be only one timing signal generation circuit 1, 2 feeding all channels. The adc, 11, would be a single adc with multiplexed inputs as all physiological signals from the body are very low frequency compared with typical multiplexer and adc response speeds.

A 4 MHz crystal 1 is used to provide high accuracy and stability timing signals via a timing generation circuit 2. This provides narrow 1 kHz rate pulses to the modulator 3, which has a current drive output modulated between a high and low but non-zero level by the pulse train. This current drive generates energy at a wavelength of 890 nm, using a gallium aluminium arsenide IR optical transmitter 5.

There is also an IR optical receiver in the form of a silicon PIN photodiode with a response range from 750 nm to 1100 nm, 6. This IR receiver is connected to a local charge to voltage convertor 7, which provides a low source impedance unfiltered broadband voltage output at the 1 kHz pulse rate.

Figure 2:
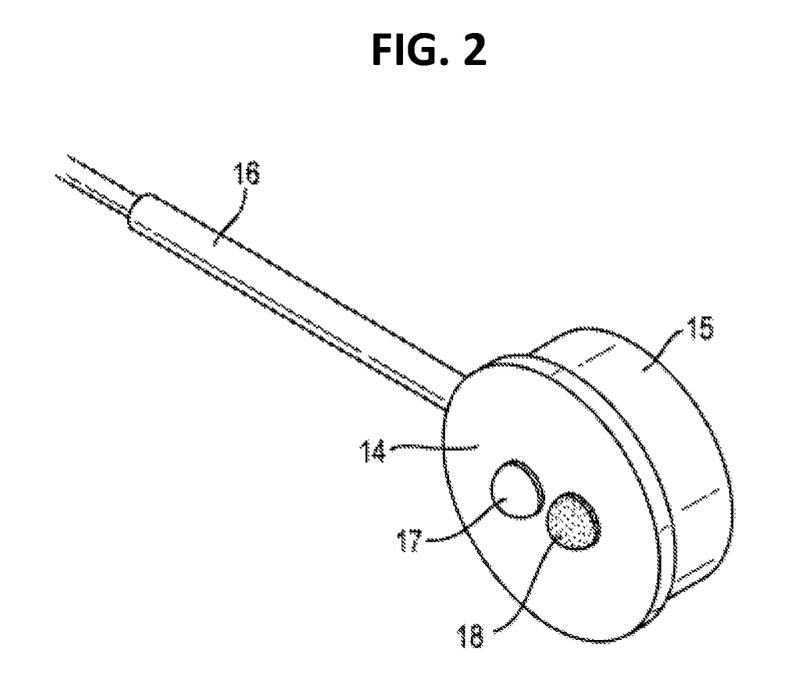
FIG. 2 is a perspective view of an illustrative transducer suitable for use with an exemplary embodiment.

With reference to FIG. 2, the IR transmitter 5, receiver 6 and charge to voltage convertor 7 are physically housed in a remote cable connected 16, transducer body 15. This has a total height of 10 mm, and consists of a cylindrical body 25 mm in diameter and with a slightly larger 28 mm diameter circular base 2 mm thick, 14. The base contains two small circular apertures within which are the tips of infra-red transmitter 18, and receiver 17, devices. These are spaced apart with a centre to centre distance 6 mm. In normal operation the transducer base is in accurate contact with skin of a patient. This provides a beam of IR energy from the IR transmitter 18, into the skin and surface tissues to depth in excess of 2 mm. Random photon to photon scattering within the beam enables much attenuated IR energy to be gathered by the IR receiver 17.

Returning to FIG. 1, the charge to voltage convertor 7, output is fed to a synchronous receiver circuit 8, timed by the same 1 kHz pulse train used to drive the current modulator 3. This synchronous receiver provides a broadband unfiltered output. An analogue high pass filter 9, two pole Sallen and Key, −3 dB at 0.07 Hz, is used to remove the dc and very low frequency signal component. This would otherwise use up the majority of the adc dynamic range and lower effective resolution for the higher frequency physiological frequencies of interest. Anti-aliasing is provided by an analogue low pass filter 10, two pole Sallen and Key, −3 dB at 6 Hz.

The filtered baseband signal is fed to an adc 11, with the digital output used for all other signal processing within a conventional microprocessor system which is not shown in detail.

Figure 3:
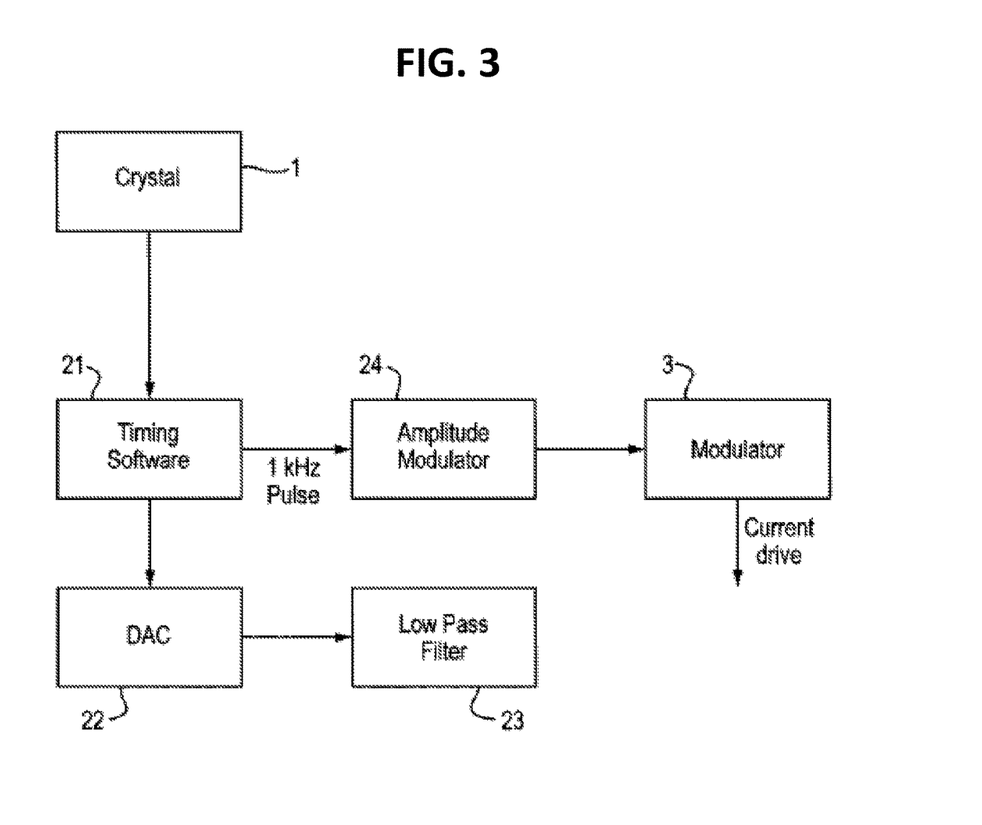
FIG. 3 is a schematic block diagram showing modifications to the system of FIG. 1 for adding a compensation signal in accordance with an embodiment.

With reference to FIG. 3, in order to add a compensation signal to the system, only parts of the circuit providing current drive to the IR transmitter need to change. The same crystal 1 now provides timing to a modified timing generation circuit. This consists of PIC microcontroller implementing timing in software 21 rather than hardware and containing an integral 12 bit digital-to-analogue convertor (dac) 22. A 1 khz pulse train is generated as before via a digital output port but also a digital sine wave representation. This is fed to the integral dac at a 20.48 kHz update rate. The dac output is low-pass filtered, single pole R-C, −3 dB at 20 Hz, to remove update rate components and provide a clean sine wave at exactly 5 Hz. This is fed together with the 1 kHz pulse stream to a new amplitude modulator 24.

This provides a 1 kHz pulse stream, now amplitude modulated at 5 Hz to the same current drive modulator 3 as before. The sine wave amplitude, and therefore the amplitude modulation depth is adjusted in healthy volunteer testing to use up no more than 5% of the analogue-to-digital converter (adc) dynamic range. This ensures that this compensation signal addition does not significantly decrease the adc resolution for the physiological signal components of interest.

For two or more transducers there would only be a single system (1, 21, 22, 23, 24) supplying an amplitude modulated 1 kHz pulse stream to the individual channel current modulators 3.

The effect of this is to provide a phantom physiological signal at 5 Hz in the receive system, but one of known and identical original amplitude for all channels. Since 5 Hz is within the filter pass band range used, it passes relatively unaffected through to the digital domain via the adc as a narrow energy spectral density distribution centred at 5 Hz.

Figure 4:
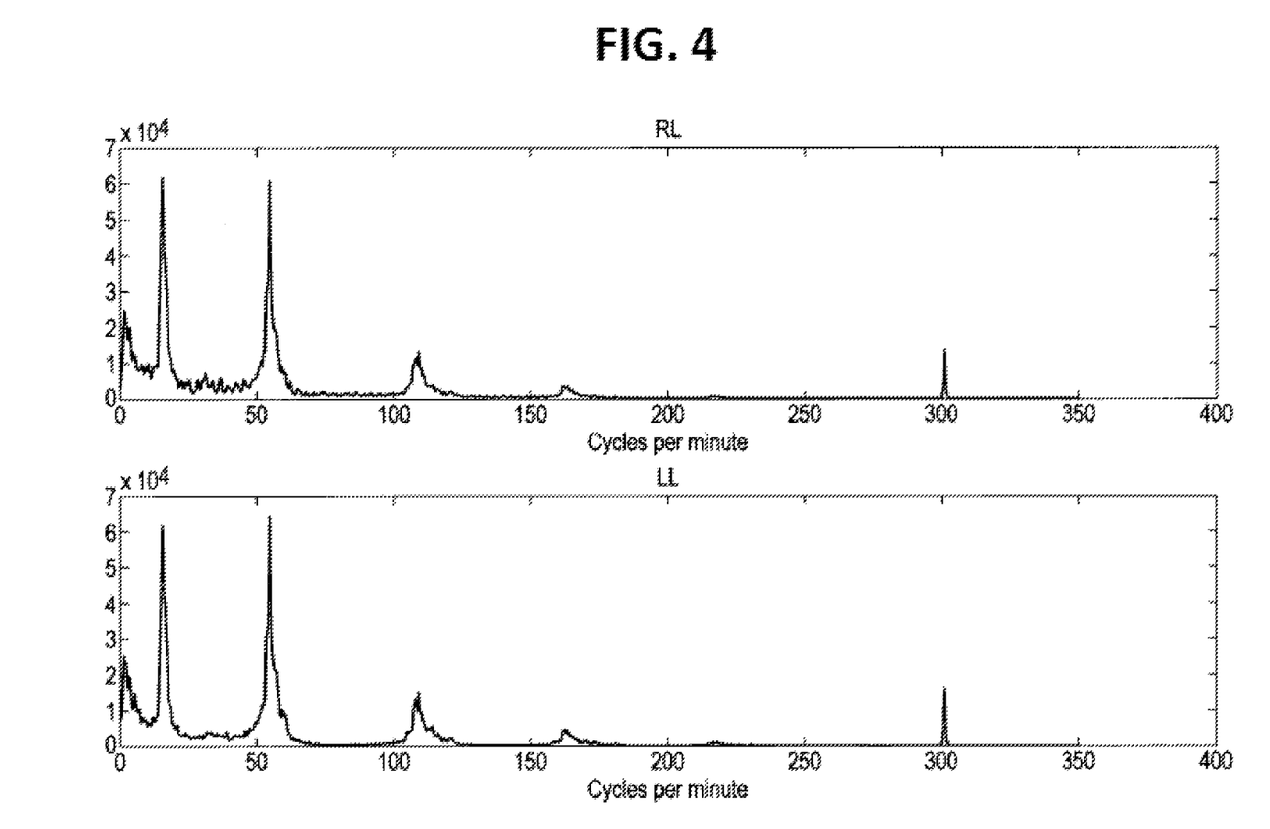
FIG. 4 is a pair of graphs respectively showing recovered baseband energy spectral density including a compensation signal in left and right channels.

FIG. 4 shows the result of applying a Fast Fourier Transform (FFT) to a typical single channel adc digital output from each of two transducers below the knee on the right (plot RL) and left (plot LL) respectively. The FFT was 64 k point performed on a six minute data record using a Hamming window and the results are shown graphically in arbitrary energy units (y axis) versus frequency in cycles per minute (x axis). The key energy spectral density variations are easily categorised by inspecting the energy peaks reading from right to left:

(a) at 300 bpm, the 5 Hz compensation signal;
(b) at approximately 165 bpm, the second harmonic of the cardiac rate;
(c) at approximately 110 bpm, the first harmonic of the cardiac rate;
(d) at approximately 55 bpm, the cardiac rate fundamental;
(e) at approximately 15 bpm, the breathing fundamental frequency; and
(f) below 15 bpm, low frequency energy from vasomotor effects.

The 5 Hz compensation signal component can easily be removed from this overall signal without affecting any other physiological component of interest by digital band pass filtering. A first order Butterworth digital band-pass filter is used, centre frequency 5 Hz and bandwidth 0.5 Hz. The data record is filtered in each direction to remove the time delay effects of the filter. This action is repeated four times to give an overall effect approximately equivalent to an eighth order filter.

EXAMPLES

By way of an example, consider the situation of a pair of such optical sensors located 100 mm above the medial malleolus on the left and right legs of a patient.

Let the signal from the left-leg transducer, after 5 Hz component removal, be Sle(t).

Let the signal from the right-leg transducer, after 5 Hz component removal, be Sri(t).

Let the 5 Hz component amplitude extracted from the left-leg overall transducer signal be 5le.

Let the 5 Hz component amplitude extracted from the right-leg overall transducer signal be 5ri.

Then multiply Sri(t) by 5le/5ri to form SriComp(t).

Sle(t) and SriComp(t) are now compensated for the differences in transmit and receive hardware tolerances, as well as differences in effective attenuation between the IR optical paths of the left and right leg transducers.

Note that the signals 5le and 5ri can be either instantaneous single samples or averaged over variable but identical time periods up to the complete duration of Sle(t) and Sri(t), to suit the result required.

The invention claimed is:

1. An apparatus for compensating for a differential error between a plurality of body surface sensors for acquiring respective physiological signals from a human or animal patient, each such sensor respectively comprising a transmitter, a receiver, and a charge-to-voltage converter connected to an output of the respective receiver, the apparatus comprising:
   a timing signal generator comprising an oscillator, to generate a timing signal;
   a channel for each respective body surface sensor, the channel comprising:
      (i) a current modulator to receive said timing signal and supply a current drive signal timed by said timing signal to the transmitter of the respective body surface sensor;
      (ii) a synchronous receiver to receive said timing signal from the timing signal generator and an output signal timed by said timing signal from the charge-to-voltage converter of the respective body surface sensor and supply a broadband output signal;
      (iii) an analogue high-pass filter to receive the broadband output signal from the synchronous receiver and supply a filtered output signal; and
      (iv) an anti-aliasing analogue low-pass filter to receive the filtered output signal from the high-pass filter and supply an anti-aliased output signal;
   the apparatus further comprising:
      an analogue-to-digital converter to receive the anti-aliased output signal from the respective channel of each respective body surface sensor and supply a digital output signal for downstream signal processing;
      wherein the timing signal generator also generates a digital representation of a sine wave and comprises a digital-to-analogue converter to receive the digital sine wave representation at an update rate higher than a frequency of the timing signal and convert the digital sine wave representation into an analogue sine wave having a frequency greater than a highest frequency of the physiological signals and less than a cut-off frequency of the anti-aliasing low pass filter;
      a low-pass filter to receive the analogue sine wave from the digital-to-analogue converter and remove update rate components therefrom to provide a clean sine wave; and
      an amplitude modulator to receive the clean sine wave from the low-pass filter and add the clean sine wave to the timing signal.

2. An apparatus according to claim 1, wherein the oscillator is a crystal with a natural frequency substantially equal to 4 MHz.

3. An apparatus according to claim 1, wherein the timing signal generator generates a timing signal with a frequency of from 500 to 1500 Hz.

4. An apparatus according to claim 1, wherein the timing signal generator generates a timing signal with a frequency of from 500 to 1500 Hz.

5. An apparatus according to claim 1, wherein the timing signal generator generates a timing signal with a frequency substantially equal to 1 kHz.

6. An apparatus according to claim 1, wherein the analogue high-pass filter is a two-pole, Sallen-Key filter providing 3 dB at about 0.07 Hz.

7. An apparatus according to claim 1, wherein the anti-aliasing analogue low-pass filter is a two-pole, Sallen-Key filter providing 3 dB at about 6 Hz.

8. An apparatus according to claim 1, wherein the update rate is substantially equal to 20.48 kHz.

9. An apparatus according to claim 1, wherein the low-pass filter is a single-pole, R-C filter providing −3 dB at about 20 Hz.

10. An apparatus according to claim 1, further comprising the plurality of body surface sensors.

11. An apparatus according to claim 10, wherein the transmitter is a gallium aluminium arsenide infrared optical transmitter radiating energy at a wavelength substantially equal to 890 nm, and the receiver is an infrared optical receiver in the form of a silicon PIN photodiode with a response in the range of from 750 to 1100 nm.

12. A method of compensating for a differential error between a plurality of body surface sensors, where each of the plurality of body surface sensors respectively comprises a transmitter and a receiver, the method comprising:

adding an amplitude modulated signal to a transmitted signal respectively transmitted by each of said transmitters, the amplitude modulated signal having a frequency:

(i) greater than a highest frequency of a physiological signal of a human or animal patient to which the plurality of body surface sensors is applied; and (ii) less than a cut-off frequency of an anti-aliasing low pass filter of an apparatus for processing a received signal respectively received by each of said receivers;

applying a band-pass filter to recover the amplitude modulated signal from a plurality of the received signals to provide a respective plurality of compensation signals;

comparing respective amplitudes of the respective plurality of compensation signals with each other; and adjusting an amplitude of at least one of the respective received signals until the amplitudes of the respective plurality of compensation signals are substantially equal to each other.

13. A method according to claim 12, wherein the frequency of the amplitude modulated signal is greater than a second harmonic of a heartbeat of the human or animal patient.

14. A method according to claim 12, wherein the frequency of the amplitude modulated signal is from 3 to 7 Hz.

15. A method according to claim 12, wherein the frequency of the amplitude modulated signal is from 4 to 6 Hz.

16. A method according to claim 12, wherein the frequency of the amplitude modulated signal is substantially equal to 5 Hz.

* * * * *

UNITED STATES PATENT AND TRADEMARK OFFICE
CERTIFICATE OF CORRECTION

PATENT NO. : 10,390,717 B2
APPLICATION NO. : 15/365635
DATED : August 27, 2019
INVENTOR(S) : Stephen John Cook et al.

Page 1 of 1

It is certified that error appears in the above-identified patent and that said Letters Patent is hereby corrected as shown below:

In the Claims

Column 8, Line 49, Claim 6, delete "3 dB" and insert -- –3 dB --

Column 8, Line 52, Claim 7, delete "3 dB" and insert -- –3 dB --

Signed and Sealed this
Twenty-ninth Day of October, 2019

Andrei Iancu
*Director of the United States Patent and Trademark Office*